(12) United States Patent
Lemchen et al.

(10) Patent No.: US 11,284,969 B2
(45) Date of Patent: *Mar. 29, 2022

(54) SYSTEM AND METHOD FOR ORDERING AND MANUFACTURING CUSTOMIZED DENTAL APPLIANCES AND THE TRACKING OF ORTHODONTIC PRODUCTS

(71) Applicant: EasyRx, LLC., Atlanta, GA (US)

(72) Inventors: Marc Lemchen, New York, NY (US); Jim Wright, Williamsville, NY (US); Michael Wright, Clarence Center, NY (US); Todd Blankenbecler, Atlanta, GA (US)

(73) Assignee: EasyRx, LLC., Atlanta, GA (US)

( * ) Notice: Subject to any disclaimer, the term of this patent is extended or adjusted under 35 U.S.C. 154(b) by 210 days.

This patent is subject to a terminal disclaimer.

(21) Appl. No.: 16/712,362

(22) Filed: Dec. 12, 2019

(65) Prior Publication Data
US 2020/0113650 A1    Apr. 16, 2020

Related U.S. Application Data

(60) Continuation-in-part of application No. 15/856,958, filed on Dec. 28, 2017, now Pat. No. 10,548,691,
(Continued)

(51) Int. Cl.
*A61C 7/00*    (2006.01)
*G16H 20/10*    (2018.01)
(Continued)

(52) U.S. Cl.
CPC .......... *A61C 7/002* (2013.01); *G06Q 10/101* (2013.01); *G06Q 10/103* (2013.01); *G06Q 30/04* (2013.01);
(Continued)

(58) Field of Classification Search
CPC .......... A61C 7/002; G16H 10/60; G06Q 30/04
See application file for complete search history.

(56) References Cited

U.S. PATENT DOCUMENTS 6,733,289 B2    5/2004    Manemann
7,305,367 B1 *  12/2007   Hollis ................ G06Q 30/0283
                                              705/400
(Continued)

OTHER PUBLICATIONS

Website, Orthodontic Products Online, EasyRx releases its cloud-based appliance prescription management system, Oct. 15, 2012, internal pp. 1-3, www.orthodonticproductsonline.com/2012/10/orthodent-laboratory-releases-cloud-based-easyrx.

*Primary Examiner* — Vincent H Tran
(74) *Attorney, Agent, or Firm* — Marcus C. Dawes; Daniel L. Dawes

(57) ABSTRACT

A prescription management system is used by an orthodontic or dental lab and a plurality of prescribing users who send prescriptions for customized orthodontic or dental appliances to the lab. The prescriptions are stored in a database selectively accessible by the lab and plurality of prescribing users. A digital workspace is provided in the system in which the lab or prescribing users may create designs for the customized appliances. The designs of the appliances are stored in the database. A tracking record of fabrication of the appliances is stored in the database. A plurality of billings are simultaneously generated in response to the submissions and storage of the prescriptions, the designs of the customized appliances and the fabrication of the designed customized appliances.

19 Claims, 16 Drawing Sheets

Related U.S. Application Data which is a division of application No. 15/072,198, filed on Mar. 16, 2016, now Pat. No. 10,299,891.

(51) Int. Cl.
*G16H 40/20* (2018.01)
*G16H 20/40* (2018.01)
*G16H 20/00* (2018.01)
*G06Q 10/10* (2012.01)
*G16H 10/60* (2018.01)
*G06Q 30/04* (2012.01)
*G06Q 30/06* (2012.01)
*G16H 50/00* (2018.01)

(52) U.S. Cl.
CPC ......... *G06Q 30/0621* (2013.01); *G16H 10/60* (2018.01); *G16H 20/00* (2018.01); *G16H 20/10* (2018.01); *G16H 20/40* (2018.01); *G16H 40/20* (2018.01); *G16H 50/00* (2018.01)

(56) References Cited

U.S. PATENT DOCUMENTS

| | | | |
|---|---|---|---|
| 8,121,718 B2 | 2/2012 | Rubbert | |
| 8,185,417 B1 | 5/2012 | Brown | |
| 8,738,396 B2 * | 5/2014 | Green, III | G16H 10/60 |
| | | | 705/2 |
| 10,299,891 B2 * | 5/2019 | Lemchen | G06Q 10/101 |
| 10,929,904 B1 * | 2/2021 | Jacobs, II | G06Q 30/0611 |
| 2003/0163391 A1 * | 8/2003 | Elkins | G06Q 30/0625 |
| | | | 705/26.8 |
| 2004/0214128 A1 * | 10/2004 | Sachdeva | A61C 7/146 |
| | | | 433/24 |
| 2004/0265770 A1 * | 12/2004 | Chapoulaud | A61C 7/146 |
| | | | 433/24 |
| 2005/0043836 A1 * | 2/2005 | Jaworski | G06Q 30/0603 |
| | | | 700/98 |
| 2005/0080502 A1 * | 4/2005 | Chernyak | G06F 30/00 |
| | | | 700/97 |
| 2006/0078842 A1 * | 4/2006 | Sachdeva | A61C 9/0053 |
| | | | 433/24 |
| 2007/0218418 A1 * | 9/2007 | Raby | A61C 7/00 |
| | | | 433/24 |
| 2008/0033754 A1 * | 2/2008 | Smith | G16H 10/60 |
| | | | 705/2 |
| 2008/0096151 A1 | 4/2008 | Cinader | |
| 2008/0195418 A1 * | 8/2008 | Parker | G16H 15/00 |
| | | | 705/2 |
| 2009/0017410 A1 * | 1/2009 | Raby | G16H 20/40 |
| | | | 433/2 |
| 2010/0076581 A1 * | 3/2010 | Violante | A61C 13/0004 |
| | | | 700/98 |
| 2011/0288889 A1 * | 11/2011 | Jones | G06Q 40/12 |
| | | | 705/3 |
| 2014/0032233 A1 * | 1/2014 | Johnson | G16H 20/10 |
| | | | 705/2 |
| 2014/0229190 A1 * | 8/2014 | Royal | G16H 70/20 |
| | | | 705/2 |
| 2015/0332018 A1 * | 11/2015 | Rosen | G16H 10/40 |
| | | | 705/2 |
| 2016/0310235 A1 * | 10/2016 | Derakhshan | G16H 50/50 |
| 2016/0354185 A9 * | 12/2016 | Taub | G16H 20/40 |
| 2017/0020638 A1 * | 1/2017 | Stine | A61C 13/0006 |
| 2017/0279876 A1 * | 9/2017 | Prasad | G06Q 50/06 |
| 2019/0083212 A1 * | 3/2019 | Cowburn | G06F 3/015 |

\* cited by examiner easyrx

Dashboard  Patients  Templates  Prescriptions

Practice Dashboard
Dashboard

Saved Prescriptions (Not Yet Submitted)                    [Search]

| ID | Patient | Date Created | |
|---|---|---|---|
| 21354 | George Washington | 1/19/12 | view edit delete |
| 21339 | Smith John | 1/19/12 | view edit delete |
| 19463 | Don Johnson | 12/9/11 | view edit delete |
| 19462 | Michael Knight | 12/9/11 | view edit delete |
| 18715 | Internet explorer | 11/22/11 | view edit delete |
| 18714 | Internet explorer | 11/22/11 | view edit delete |
| 18542 | Spam Bohanan | 11/18/11 | view edit delete |
| 16175 | Abraham Lincoln | 9/28/11 | view edit delete |
| 16019 | Abraham Lincoln | 9/24/11 | view edit delete |
| 14538 | Abraham Lincoln | 8/21/11 | view edit delete |

‹Prev 1 2 3 Next›

Submitted Prescriptions                                    [Search]

| ID | Patient | Doctor | Date Created | Date Needed | |
|---|---|---|---|---|---|
| 18596 | John Labatts | James Wright | 11/21/11 | 1/26/12 | view |
| 9407 | John Smith | James Wright | 5/3/11 | 5/18/11 | view |
| 6859 | Mr. T | James Wright | 3/7/11 | 3/25/11 | view |
| 5429 | Jack Black | James Wright | 3/6/11 | 3/10/11 | view |

FIG. 2 easyrx

Dashboard | Patients | Templates | Prescriptions

Manage Patients
Dashboard >> Manage Patients >> View Patient

First Name: Smith     Last Name: John
Date of Birth: 5/9/93

Edit List

Prescriptions

[ Search ]

| ID | Date Created | |
|---|---|---|
| 21339 | 1/19/12 | view edit delete |

[ Create Prescription »]

File Upload(s)

Select the "Add File(s)" button or drag and drop a file (or files) on to this page to upload
[ Add File(s) »]

 21339/012345_Pre Tx_Maxillar.stl    5.62 MB 

21339/November 2011.xls    29.18 KB 

FIG. 3

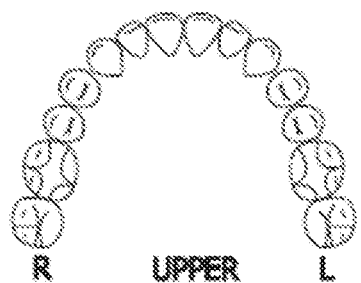
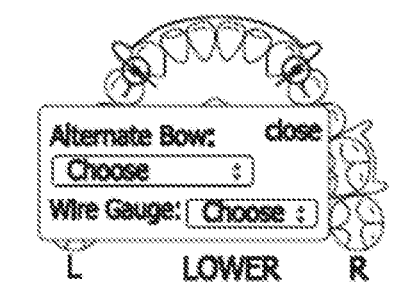
FIG. 6

Comments  Resets  Templates  Study Model  ClearLign  Uploads
FIG. 7
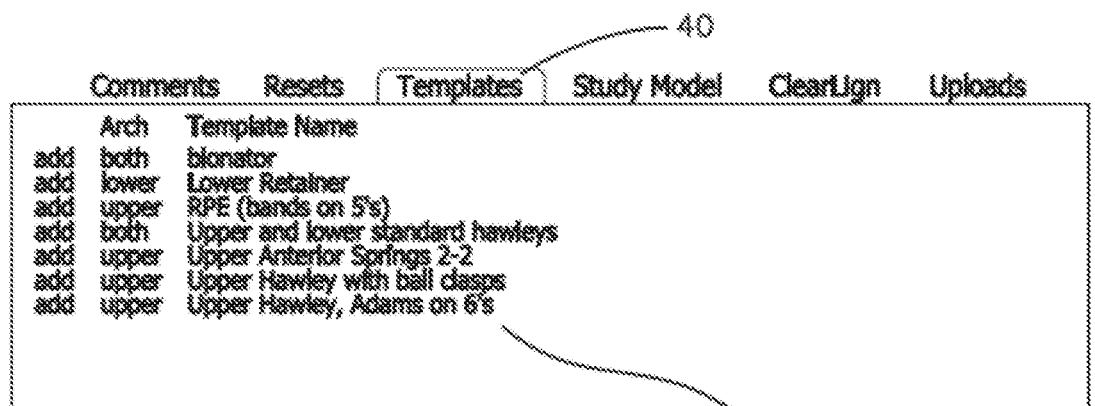
FIG. 9
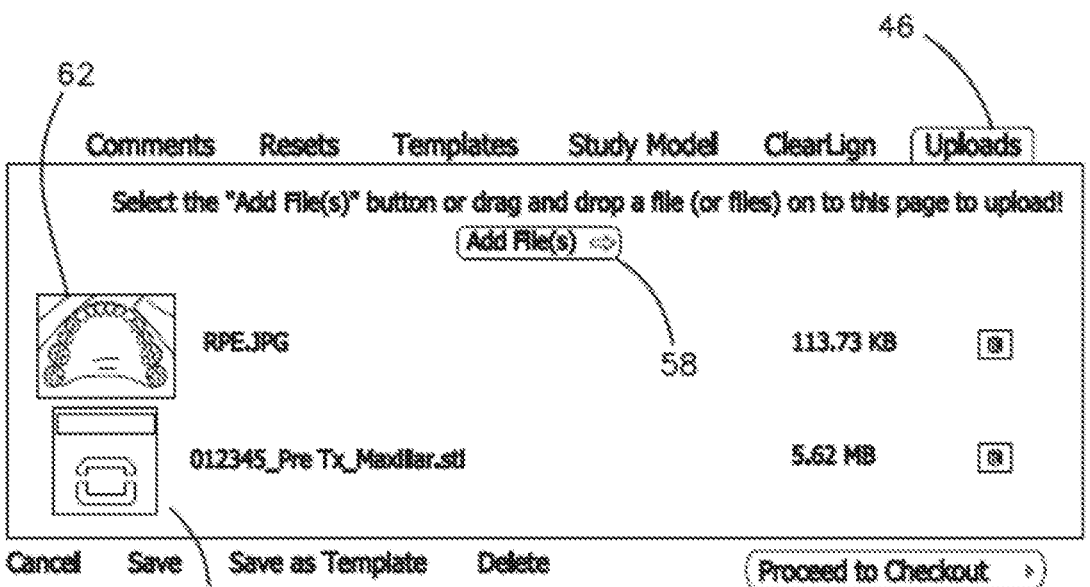
FIG. 11

Prescription Check-In
Dashboard >> Prescription Check-In

Scan the prescription barcode or type the prescription ID and click the "Submit" button to start the check-in process. If a prescription has not been created in the system use the "Written Prescription" button.

Prescription ID

[Written Prescription]

[Submit]

FIG. 13

Prescription Completion Log
Dashboard >> Prescription Completion Log

Department
[Acrylic Station]

Scan one or more prescription barcodes, or type the prescription ID.

Add Another [Submit]

FIG. 14 easyrx

Dashboard | Practices | Patients | Check-in | Check-out | QuickBooks | Prescriptions QuickBooks Export
  Shipping Report
  Archived Import File Folder QuickBooks Export
Dashboard >> QuickBooks Export

| Rx ID | Line Item | Price | QuickBooks Item Number |
|---|---|---|---|
| 15822 | Fixed 3D Quad-helix, Band and Installation | $70.65 | 4010 Sales Fixed Tax |

[Generate File]

Fixed: 3D Quad-helix, Band and Installation

| Description | Price | Quantity | Total |
|---|---|---|---|
| 3D Quad-helix | $53.25 | 1 | $53.25 |
| Band and Installation | $8.70 | 2 | $17.40 |
| | | Total | $70.65 |

FIG. 15 easyrx

Dashboard | Accounts | Parts (70) | Patients (68) | Prescriptions (66) | Templates (40)

Manage Parts
  Tree View
  Study Model & Resets
  Digital Study Models
  ClearLign
  Part Option
  Bands
  Change All Part Prices Manage Parts
Dashboard >> Manage Parts

| Part Name | Price | Status | | |
|---|---|---|---|---|
| "W" Arch | $41.60 | Active | view | edit |
| "W" Arch w/ Habit Crib | $62.90 | Active | view | edit |
| .0175 Coaxial | $25.20 | Active | view | edit |
| .0175 Coaxial w/ Tray | $60.75 | Active | view | edit |
| 3-way Expansion Screw | $39.25 | Active | view | edit |
| 3D Lingual Arch | $44.00 | Active | view | edit |
| 3D Quad-helix | $53.25 | Active | view | edit |
| 3x3 Bonded | $25.20 | Active | view | edit |
| 3x3 Krause | $61.10 | Active | view | edit |
| 3x3 w/ Bonding Tray | $60.75 | Active | view | edit |

< Prev [1] 2 3 4 5 ... 18 Next >

FIG. 16 easyrx
ALIGNER TRACKING SYSTEM

Kevin Clark / 12341234
Laboratory: Williams Orthodontics In-House Lab
Office: Atlanta
Doctor: Robert Jones

| | Upper | Lower | Total |
|---|---|---|---|
| Total number of trays | 20 | 20 | 20 |
| | | | |
| Batch #1 | | | |
| Trays in batch | 9 | 9 | 18 |
| Trays printed in batch | 9 | 9 | 18 |
| Trays delivered in batch | 9 | 9 | 18 |
| Change trays every X days | | | 7 days |
| Time in stage | | | 63 days |
| Delivery date | | | 11/14/2019 |
| Finish Date | | | 1/18/2020 |
| Reminders | | | |
| Date to print the next batch | | | 1/8/2020 |
| Date to contact patient and schedule follow up appointment | | | 12/19/2019 |

CANCEL  SAVE

SAVE BATCH

| | Upper | Lower | Total |
|---|---|---|---|
| Trays Remaining | 11 | 11 | 22 |

I'M DONE

FIG. 24

SYSTEM AND METHOD FOR ORDERING AND MANUFACTURING CUSTOMIZED DENTAL APPLIANCES AND THE TRACKING OF ORTHODONTIC PRODUCTS

BACKGROUND

Field of the Technology

The invention relates to the field of ordering, manufacturing, billing and documenting the process of customized orthodontic and dental appliances.

Description of the Prior Art

In the orthodontic laboratory, prescriptions have been traditionally provided to the lab with a graphical representation of the design of the appliance used for treatment. A typical paper prescription is filled out, with a hand drawn design and sent to the lab with a dental impression or cast for fabrication. Once received, the patient information is entered into a database and the case is scheduled for the design review. A designer reviews the paper prescription and makes any needed modifications for the technicians, who will be making the appliance and for the billing department to bill for the parts and services rendered in response to the prescription.

Once the appliance has been designed and then fabricated, the billing department makes a copy of the prescription and manually bills out the appliance. Since each appliance is made up of multiple parts with very specific designs, the bill is detailed and manually broken down to illustrate the parts of the retainer. The paper prescriptions are then filed and stored away for reference.

BRIEF SUMMARY

The illustrated embodiments of the invention include within their scope a method for using a prescription management network directly communicating a dental lab with a prescribing user. The method includes creating a digital graphical representation in a computer of a patient's teeth by the prescribing user and then creating a digital prescription for a customized dental appliance by the prescribing user applying a plurality of dental components to the digital graphical representation of a patient's teeth in a computer. Next a plurality of options associated with each of the plurality of dental components within the customized dental appliance are selected which is then submitted along with the digital graphical representation of a patient's teeth directly from the prescribing user's computer to the dental lab through the network. The digital prescription is then stored in a cloud-based database which is accessible by both the prescribing user through the prescribing user's computer and by the dental lab through the dental lab's computer. After being accessed by the dental lab through the dental lab's computer, the dental appliances within the prescription are fabricated by the dental lab at the dental lab from a predefined parts library. The fabrication of the customized dental appliance by the prescribing user or by the dental lab may be tracked by updating the cloud-based database. The method further provides for simultaneously creating at the dental lab's computer an automatic billing and storing the automatic billing in the cloud-based database at the same time the digital prescription is created by the prescribing user, when the plurality of options associated with each of the plurality of dental components within the customized dental appliance are selected, when the digital prescription is submitted directly to the dental lab by the prescribing user, when the digital prescription is stored, when the customized dental appliance is designed by the dental lab, or when the designed customized dental appliance is fabricated by the dental lab, regardless of whether initiated through either the prescribing user's or the dental lab's computer. It should be noted that simultaneously creating the billing and storing the billing in the cloud-based database at the same time the digital prescription is created by the prescribing user specifically includes creating an itemized queue of the applied plurality of dental components along with their selected plurality of options and their respective pricing automatically through either the prescribing user's or the dental lab's computer in real time as each dental component is applied to the digital graphical representation of the patient's teeth by the prescribing user.

In a specific embodiment, each of the method steps for using the prescription management network are performed by issuing a plurality of voice commands by the prescribing user.

In one particular embodiment, selecting from a plurality of options associated with each of the plurality of dental components within the customized dental appliance includes selecting a shade associated with at least one of the plurality of dental components, selecting a margin associated with at least one of the plurality of dental components, or selecting a pontic associated with at least one of the plurality of dental components. Here, selecting a shade associated with at least one of the plurality of dental components may specifically include selecting an occlusal, an incisal, a gingival, a stump, or a characteristic shade.

In another embodiment, the method also includes creating a customized option associated with at least one of the plurality of dental components within the customized dental appliance.

In one specific embodiment, creating a digital graphical representation in a computer of a patient's teeth by the prescribing user includes acquiring a three dimensional scan of the patient's teeth and then applying the three dimensional scan to the digital graphical representation in the computer.

In a separate but related embodiment, creating a digital prescription for a customized dental appliance by the prescribing user applying a plurality of dental components to the digital graphical representation of a patient's teeth in a computer includes creating a three dimensional digital prescription for the customized dental appliance.

The current invention further provides a method of providing an orthodontic aligner prescription tracking management network which includes an orthodontic or dental lab and at least one prescribing user. The method includes providing a digital aligner tracking workspace in a computer wherein the orthodontic or dental lab or the at least one prescribing user may access the digital aligner tracking workspace and then creating a digital prescription for a customized orthodontic aligner appliance by the prescribing user for a patient's teeth in a computer wherein the digital prescription includes a plurality of trays. Next, the digital prescription is stored in a cloud-based database which is selectively accessible by the orthodontic or dental lab and the at least one prescribing user. A record of the status of the digital prescription for the customized orthodontic aligner appliances is tracked and stored and the digital prescription may be updated by either the orthodontic or dental lab or the at least one prescribing user. At the same time the digital prescription for the customized orthodontic aligner appliance is created by the prescribing user for a patient's teeth in the computer, or when the digital prescription is stored, or when the digital prescription is updated, a billing is created in the cloud-based database regardless if updated by either the orthodontic or dental lab or the at least one prescribing user. Additionally, tracking and storing a record of the status of the digital prescription for the customized orthodontic aligner appliances specifically includes automatically updating the record of the status of the digital prescription according to any updates made to the digital prescription by either the orthodontic or dental lab or the at least one prescribing user.

In one embodiment, tracking and storing a record of the status of the digital prescription for the customized orthodontic aligner appliances also includes tracking and storing both the amount of trays that are selected from the total number of trays to be within a first batch, and the number of trays which are designated for the upper teeth and lower teeth of the patient, respectively. In this embodiment, the number of trays selected to be within the first batch that have been printed or delivered by the orthodontic or dental lab may also tracked.

In another embodiment, updating the digital prescription by either the orthodontic or dental lab or the at least one prescribing user includes adjusting a duration for each of the plurality of trays which are to be used by the patient, and then automatically updating a total duration that the plurality of trays will be used by the patient according to the adjusted duration for each of the plurality of trays. Here, a reminder to begin printing a sub-plurality of the plurality of trays according to the updated total duration that the plurality of trays will be used by the patient may also be generated.

The invention further provides a prescription management system which includes an orthodontic or dental lab and a plurality of prescribing users. The system includes means for creating a plurality of prescriptions by applying at least one dental appliance to a graphical representation of a patient's teeth by each of the plurality of prescribing users, each of the plurality of prescriptions comprising at least one dental appliance. The system also includes a cloud-based database which is configured to receive the plurality of prescriptions directly from the plurality of prescribing users, the cloud-based database itself being selectively accessible by both the plurality of prescribing users and by the orthodontic or dental lab. A digital workspace within the system is configured to provide the orthodontic or dental lab or the plurality of prescribing users the ability to customize the at least one dental appliance within each of the plurality prescriptions by selecting from a plurality of corresponding options for the at least one dental appliance. The cloud-based database is configured to store the plurality of prescriptions as well as to track and store a record of fabrication of the at least one customized dental appliance for each of the plurality of prescriptions by the orthodontic or dental lab. Additionally, the digital workspace is configured to simultaneously create a plurality of corresponding billings in the cloud-based database at the same time the plurality of prescriptions are created by the plurality of prescribing users, when the plurality of prescriptions are submitted directly by the plurality of prescribing users, when the plurality of corresponding prescriptions are stored, when the at least one dental appliance for each of the plurality of prescriptions is customized, or when the at least one dental appliance for each of the plurality of prescriptions is fabricated at the orthodontic or dental lab, regardless if initiated by either the orthodontic or dental lab or the plurality of prescribing users. More specifically, the digital workspace creates an itemized queue of the at least one applied dental appliance and its respective pricing automatically as the at least one dental appliance is applied to the graphical representation of the patient's teeth by each of the plurality of prescribing users for each of the plurality of corresponding prescriptions.

In one particular embodiment, the digital workspace includes means for selecting a shade associated with at least one of the plurality of dental components, means for selecting a margin associated with at least one of the plurality of dental components, or means for selecting a pontic associated with at least one of the plurality of dental components. In a related embodiment, the means for selecting a shade associated with at least one of the plurality of dental components specifically encompasses means for selecting an occlusal, an incisal, a gingival, a stump, or a characteristic shade.

In another embodiment, the system also includes means for creating a customized option associated with at least one of the plurality of dental components within the customized dental appliance.

In yet another embodiment, the system further includes means for issuing a plurality of voice commands by the prescribing user.

It is a further aspect of the invention that the means for creating a plurality of prescriptions by applying at least one dental appliance to a graphical representation of a patient's teeth by each of the plurality of prescribing users includes means for applying at least one dental appliance to a three dimensional scan of the patient's teeth, and relatedly, means for creating a plurality of three dimensional digital prescriptions by applying at least one dental appliance to a three dimensional scan of the patient's teeth.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIGS. 1a and 1b hand sketches created by an orthodontist for an upper and lower retainer respectively and FIGS. 1c and 1d are the corresponding customized designs created by the designer in the lab in response to the orthodontist's hand sketched prescription.

FIG. 2 is an illustrative example of a screen shot of the Practice Dashboard of the illustrated embodiment.

FIG. 3 is an illustrative example of a screen shot of the Manage Patients module of the illustrated embodiment.

FIG. 6 is an illustrative example of a screen shot of a prescription for a specific patient as used in the illustrated embodiment.

FIG. 7 is an illustrative example of a screen shot of the action tabs provided below the canvas as used in the illustrated embodiment.

FIG. 9 is an illustrative example of a screen shot of the Templates action tabs provided below the canvas as used in the illustrated embodiment.

FIG. 11 is an illustrative example of a screen shot of the Uploads action tabs provided below the canvas as used in the illustrated embodiment.

FIG. 13 is an illustrative example of a screen shot of the Prescription Check-In as used in the illustrated embodiment.

FIG. 14 is an illustrative example of a screen shot of the Prescription Completion Log as used in the illustrated embodiment.

FIG. 15 is an illustrative example of a screen shot of the Confirmation Screen as used in the illustrated embodiment.

FIG. 16 is an illustrative example of a screen shot of the administrative screen relating to the Manage Parts module as used in the illustrated embodiment.

FIG. 24 is an illustrative example of a screen shot of the aligner tracking workspace of the illustrated embodiment.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

The illustrated system and method, offered under the commercial name, Easyprescription™, is a web based application that is designed to create and manage orthodontic laboratory prescriptions within a dental clinic as well as the lab. The system coordinates and facilitates processing of orthodontic prescriptions and their fulfillment between a multiplicity of dental offices or clinics and a multiplicity of orthodontic or dental labs. In one sense, it is a digital delivery method for orthodontists to prescribe and manage their prescriptions and send them directly to the laboratory, but also a laboratory management system for the lab's processing and business transactions.

Figure 1A:
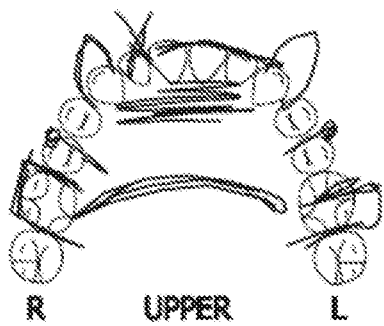
FIGS. 1a-1d are depictions of the graphic portion of a prescription for an orthodontic appliance.
Figure 1C:
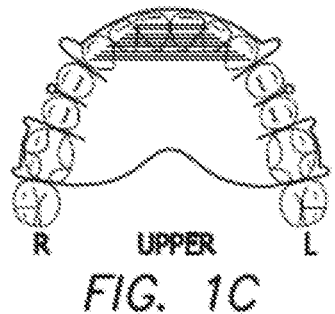
Figure 1B:
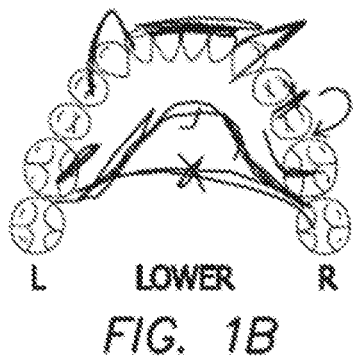
Figure 1D:
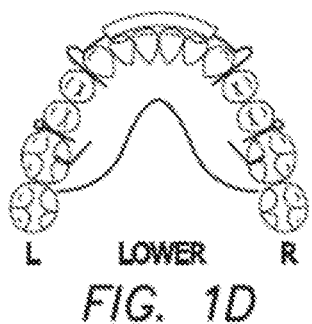

The illustrated system and method can be understood by turning to the prescription as depicted in FIGS. 1a-1d. FIGS. 1a and 1b are hand sketches created by an orthodontist for an upper and lower retainer respectively and FIGS. 1c and 1d are the corresponding customized designs created by the doctor on a computer or by a designer in the lab in response to the orthodontist's hand sketched prescription. The prescription can be created in two areas of the system, either directly from a doctor's digital or computer account or manually entered by the lab, if a paper prescription is received. A doctor or his or her staff member, included among the users of the system and method, navigates to a web portal established by the lab via an internet browser and logs into the appropriate account.

The user is presented with the Practice Dashboard 10 for their account as shown in FIG. 2 which outlines what cases are saved, waiting to be submitted to the lab, and those that have already been submitted to the laboratory. Note that the tabs 12, 14 and 16 at the top allow the user to navigate to a patient's manager, a template manager, and a prescription manager module respectively.

In order to enter a prescription for a patient, the user first needs to click the patient tab 12 and create a patient profile. Once a patient's profile is created, the user can upload any files associated with the patient or can create a prescription. A prescription can be created from an existing patient's profile. As depicted in FIG. 3 showing the display of the Manage Patients screen 18, the patient profiles includes all the information, from all the patient's prescription to any uploaded files that have been associated in any of the patient's prescriptions. The user may wish to create a prescription by clicking on button 20 and thus be taken to the prescription workspace 22 depicted in FIG. 4.

Figure 4:
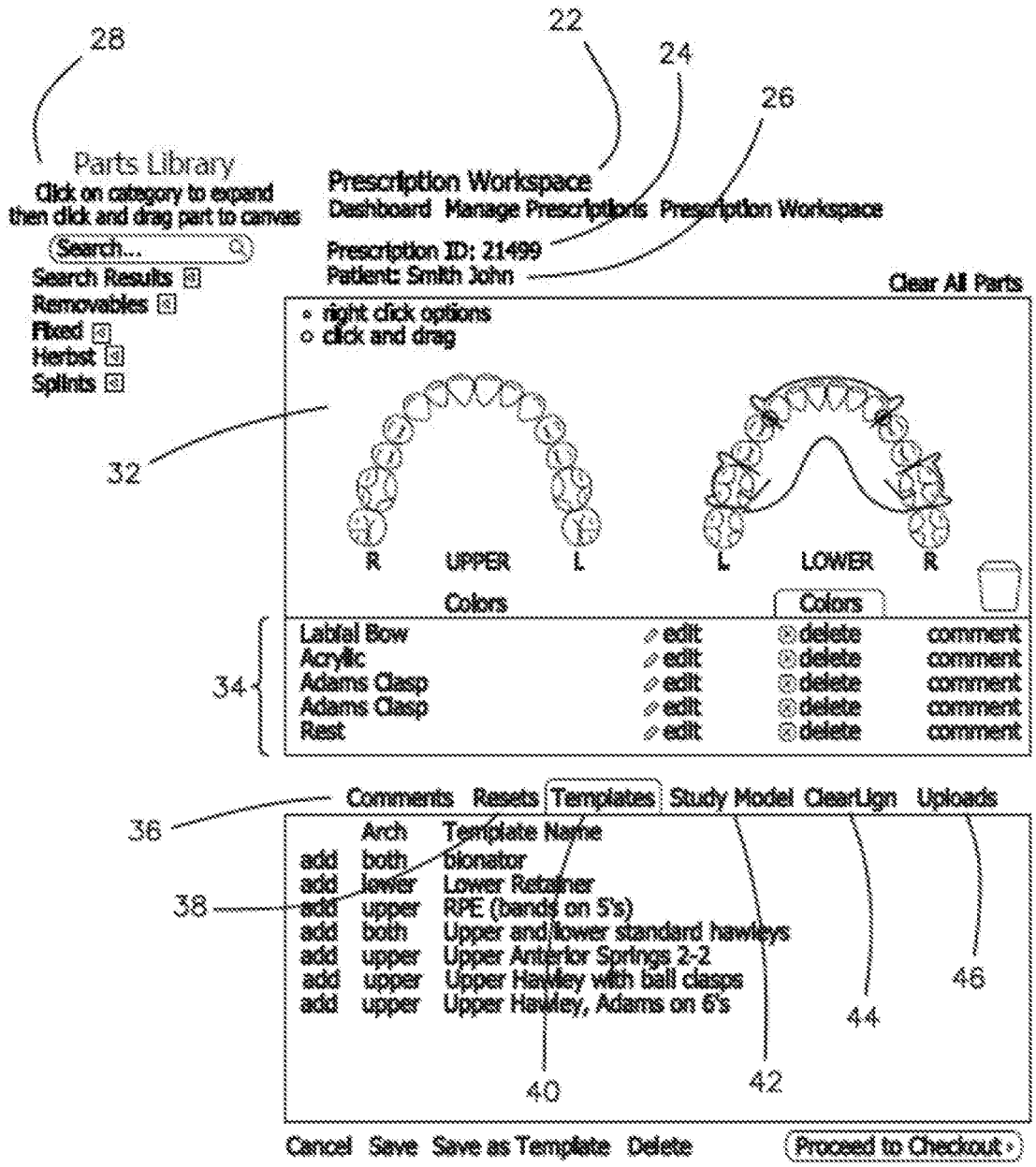
FIG. 4 is an illustrative example of a screen shot of the Prescription Workspace of the illustrated embodiment.
Figure 5:
FIG. 5 is an illustrative example of a screen shot of the Parts Library of the illustrated embodiment, illustrating in this example the pull down listing of the Clasping part.

The prescription workspace 22 is the area for any user doing any designing or modification to a prescription. The user interface is very visual and interactive to draw the user into the app. There is the prescription ID 24 which is unique to the prescription and the patient's name 26. On the left edge of the workspace screen is the parts library 28. The user opens the drop down parts listings 30 as illustrated for clasping in FIG. 5 and has the ability to click and drag all the parts of the dental appliance needed to create a complete appliance onto the canvas 32 to the right. Every part is categorized based on the parts category and can be edited from the administrative section which the lab controls. The canvas 32 is the portion of the display where the parts are graphically shown as they populate the design. In the illustration of FIG. 4, a lower retainer is being created in a graphical form, outlining every aspect of design. The user can click and drag any part on the canvas 32 by its blue handle to any area that is anatomically correct. Each part can be customized to only go in certain areas as certain parts would not make sense or appropriate if applied to certain teeth. To enhance customization, the user can right click on a part that has a red dot which enables or displays an option box 48 tailored to that part in those situations as shown in FIG. 6, where that part cannot be represented visually or it is not efficient to do so. The illustrated embodiment of the system disables the browser's right click option to accommodate the right click operation of the application.

It is important to note that while the canvas 32 seen in FIG. 4 depicts the upper and lower teeth as a two dimensional representation or object, in a related embodiment the canvas 32 may depict the upper and lower teeth of the patient as a three dimensional model or image. The three dimensional image may be a generic or standard graphical representation of a patient's teeth, or alternatively, a three dimensional image or scan may be taken directly from the patient and then uploaded to the canvas 32 to provide a three dimensional representation that is patient specific on which to apply orthodontic or dental appliances, thereby building a three dimensional prescription which is specifically altered or customized for that particular patient.

Below the canvas 32 is a queue 34 of all the selected parts and below the queue 34 are more action tabs 36-46 as shown in FIG. 7. Comments entered through comment tab 36 are date stamped and marked with the user's name, who is leaving the comment to allow for transparency of who is submitting the comment.

Figure 8:
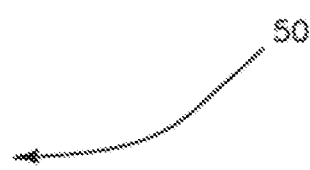
FIG. 8 is an illustrative example of a screen shot of the Resets action tabs provided below the canvas as used in the illustrated embodiment.

The resets tab 38 is a user interface for clinical movement of teeth. The user may click along what is known as the orthodontic crosshatch 50, which is a scientific numbering outline for the teeth as illustrated in FIG. 8. The display is interactive by allowing clicking on the crosshatch 50 to identify what tooth needs to be reset.

The study model tab 42 is made up of check boxes and drop downs (not shown) for clinical study model prescribing, since there is not an efficient way to graphically represent clinical study model prescribing.

The template tab 40 is a useful feature on canvas 32 as illustrated by FIG. 9. The doctor can name and create a template in the template manager 52 and save the design which appears through the use of the template tab 40 below canvas 32. The user finds the template and the user's design automatically loads on the canvas 32. This saves from clicking and dragging all the parts to the canvas 32 which saves significant time in designing.

Figure 10:
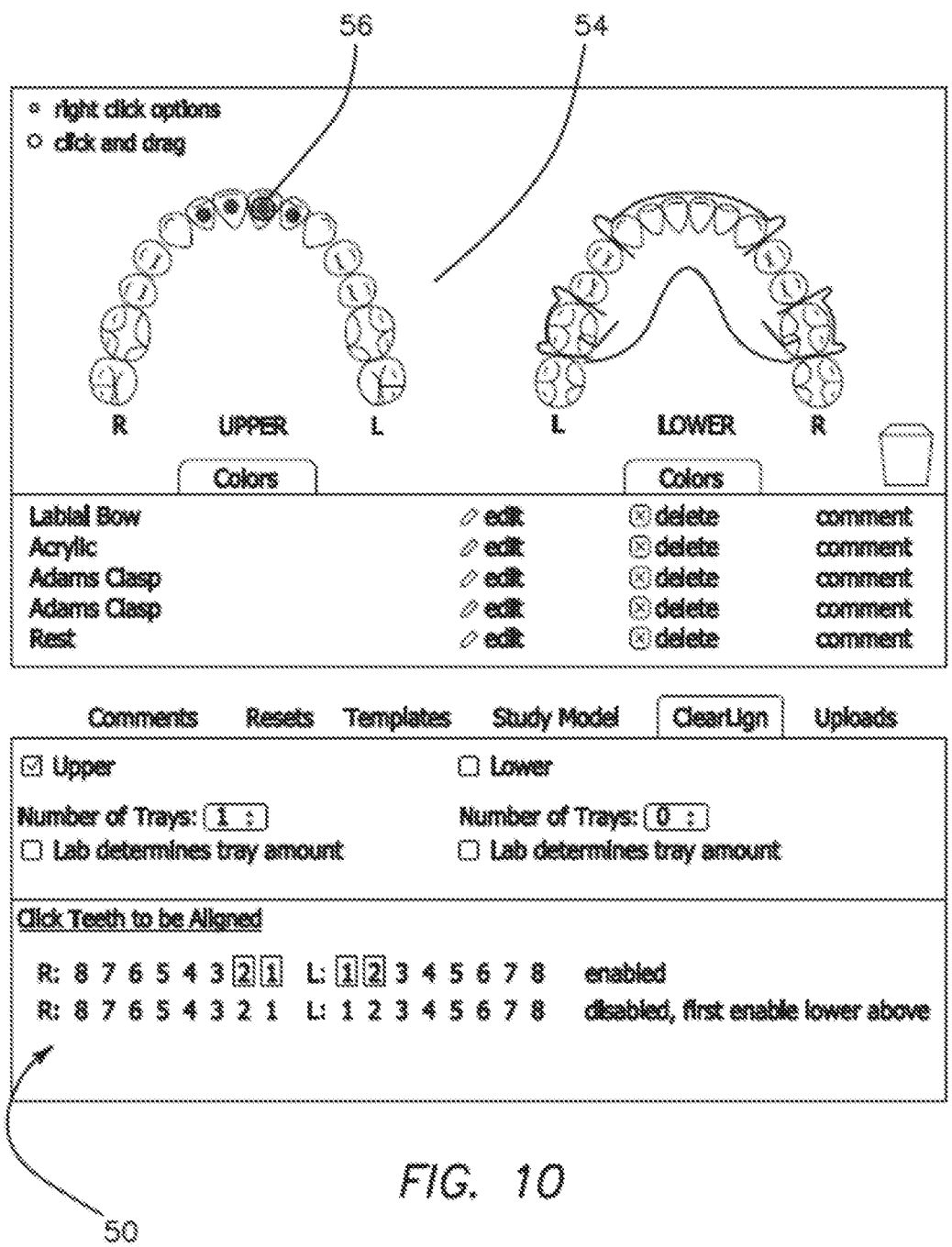
FIG. 10 is an illustrative example of a screen shot of the ClearLign action tabs provided below the canvas as used in the illustrated embodiment.

The clearlign tab 44 is a clear aligner prescription area 54 depicted in FIG. 10. The illustrated embodiment system provides a result similar to the Invisalign® approach, where a plurality of clear trays are manufactured to be applied in a sequence to align the teeth. The crosshatch 50 previously mentioned is used below the clear aligner prescription area 54 in the illustrated embodiment as the doctor picks which teeth to move. A green dot 56 on the teeth is visually present for the technician to fabricate the corresponding tray. The doctor picks how many trays are to be used or allows the lab to make the determination, and the presently illustrated system automatically bills it out properly based on the input.

The upload tab 46 is shown in FIG. 11. A user can click the "add files" button 58 or can click and drag a file or multiple files directly into the drop zone 60 and the file uploads into the prescription from digital three dimensional model files including thumbnail pictures 62 to help diagnose a case. Since everything on the canvas 32 is digital relating to the parts which are dragged into the canvas 32 from the option boxes available, everything has a price attached to it so in essence, the designer of a case is also simultaneously billing the case as the steps of making the design are performed, thereby eliminating the need to have billing manually performed separately by another worker.

Figure 12:
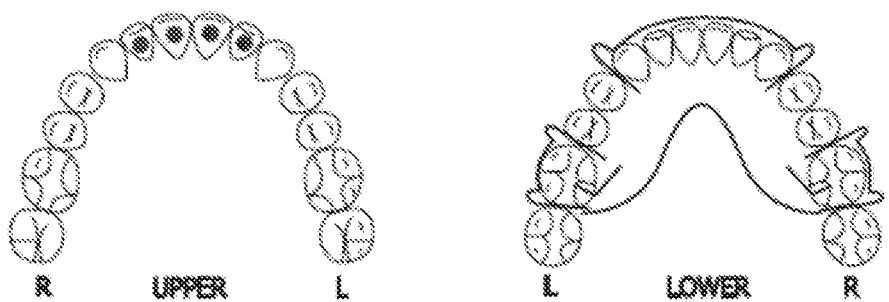
FIG. 12 is an illustrative example of a screen shot of the Confirmation Screen as used in the illustrated embodiment.

Once the case is finished or the customized appliance is completed, the user proceeds to checkout, fills out needed information on the next page about the case and logistics concerning shipping, and then is taken to the confirmation page shown in FIG. 12. The doctor prints out the prescription and sends it with the impression or the cast. At this moment, there is now a digital prescription created and documented. This prescription is now in a queue for cases waiting arrival of the model and impression at the lab.

In another embodiment, the doctor has the ability to create and export a PDF of the prescription for his or her records as shown by activation of button 64 in FIG. 12. With the use of digital scanning, the doctor will upload the digital model, design the appliance, and have the model and the prescription immediately delivered digitally for fabrication, instead a physically delivering an impression. The case is now accessible from the doctor dashboard in the submitted cases queue. This case can always be searched by it's unique ID number 24 or by name 26.

As the case is scanned in at the lab and goes through the process, the dates of interest are populated, such as the estimated ship date, on the prescription. The template manager can be accessed from the template tab 40 at the top of the screen as shown in FIG. 16. It leads the user to the workspace where the doctor can design a template instead and save it for easy retrieval on the workspace when creating a case. The user can edit and delete existing templates as well.

The prescription tab 66 at the top of the screen in FIG. 16 is a queue of all the prescriptions created by the doctor.

In summary, consider now the work flow as facilitated by the illustrated embodiment. When a user logs into a clerical account through accounts tab 68 in FIG. 16 the user is presented with a dashboard which has three queues: Submitted cases (in transit to the lab), checked in cases, and checked out cases related to the user. When a prescription comes to the lab, it is either in the digital printed form as described above, or is written on a traditional prescription for those not engaging in the computerized submission process of the illustrated system, offered under the commercial name, Easyprescription™ Easyprescription™ is used to digitize all prescriptions so a digital workflow tracking takes place. In the case of a written prescription, the data is manually input that otherwise would have been inputted by the doctor creating a new id number 24 and a digital prescription is input through the prescription check-in as shown in FIG. 13. Once the case has been logged in by the clerical account and all the information for the lab has been entered, the case is ready for review of the design if sent in by a doctor, or transferring a design from the paper prescription to the digital prescription. A user logs into the designing account where the designer can review the designs and redesign a case that came in via a paper prescription on the prescription workspace. Changes are made instantly and can be seen by any party who has access to the prescription. The designer has the ability to add charges and discounts to any prescription based on custom orders or a repair that needs a specific amount charged to the case. The designer is now acting as the biller.

Once the design is set, the case travels through the production system. A technician has the ability to log into their technician account where he or she can view cases and his or her designs to produce the needed parts via a monitor and a computer. Cases are scanned by the technician as well into their account for two reasons: 1. To physically track the case throughout the process (where is the case in the lab); and 2. To enable the system to keep track of the production of the employee which can be monitored and used for production metrics via the reporting area in the administrative account.

Once the case is completed it is ready to be check-out as depicted in FIG. 14. The clerical account bar codes the case and checks the case out. That puts the case in a Quick- Books® or accounting queue indicating that it is ready to be exported. The clerical user has the ability to hover the mouse cursor over a case and see the breakdown of the pricing structure in a drop down display as shown in FIG. 15. When all the cases have been scanned and checked out, they will reside in the QuickBooks® queue. The data here can be used to estimate the amount of sales going out as well as provide an organized shipping report. Once the clerical user clicks the "generate file" button, a .csv file is stored within their account which can be downloaded and imported into Quick-Books® via bridge software or directly into QuickBooks®.

The administrative account controls the system and allows the user to make changes to vital portions of Easyprescription™. The user can edit and delete prescriptions as well as patient profiles and run reports on departments and technicians. The user is presented with the same dashboard to see the in-coming cases, the submitted cases, as well as the checked-out cases. The user has the ability to create, edit, and delete all the user accounts within the system. The user has full control over the parts within the system, e.g. the user can change the price as well as how the parts present themselves in the parts library for those working within the workspace through the use of the Manage Parts module 70 as shown in FIG. 16. The user can globally change prices throughout the system and has access to all the prescriptions as well as the patient profiles for any doctor within the system.

The system manufactures dental products or fills orthodontic prescriptions for orthodontic appliances from several hundred parts. Each part has complex movements and several images associated with it. The system uses a native computer language to define each of the parts and their movements. For example, to specify what arches or what teeth onto which a part may move, what sub-parts of a part can be removed in any given instance, how one sub-part moves in relation to another sub-part of the same part, whether a part flips, as with springs, or what options are available to a part comprises a noninclusive listing of some of what constitutes the definition of a part and its movements. Not only does the native computer language define the movements, but with its images it creates a graphic representation of each part. With this native computer language with its definition of the parts, a very comprehensive taxonomy of orthodontic parts and appliances has been assembled. The above software definition of the parts has utility beyond the illustrated embodiments, especially as orthodontic labs work toward integrating CAD and CAM into their workflows.

One of the advantageous features of the illustrated embodiment of the system is that digital three dimensional model files are viewed using the disclosed software system from inside of a browser without installing any local software. There is no need to download software to view three dimensional models. Whether the image file is from an intra-oral scanner, cone-beam or from a digital study model service from a lab, the illustrated system provides a fast and efficient solution to view the files.

EasyRx utilizes a domain-specific language (DSL) or the native computer language for defining part movements and behaviors. An EasyRx part is a representation of an orthodontic appliance that will have different configurations and will be able to be placed in different positions in a patient's mouth. The DSL defines those available configurations and acceptable movements. Only those configurations that have a real-world applicability are allowed.

Figures 17A, 17B:
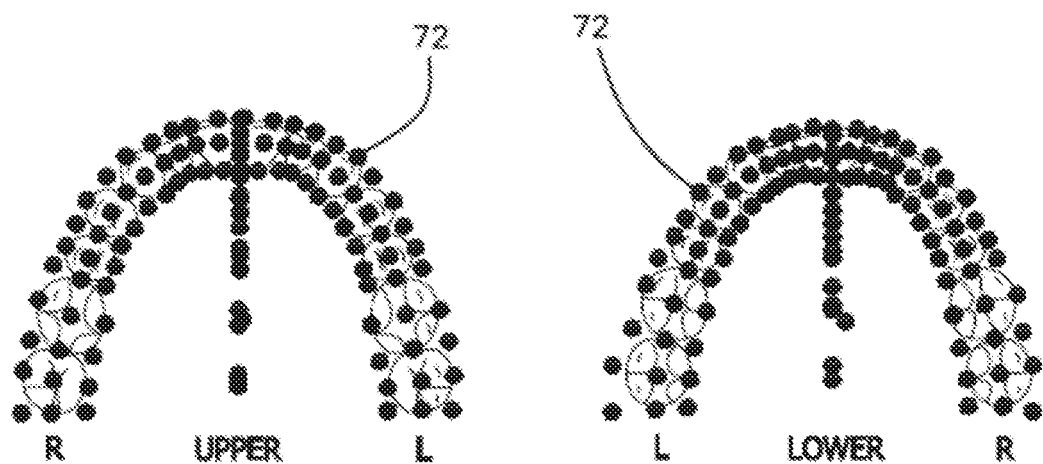
FIGS. 17a and 17b illustrate the magnet points at which anchors may be placed relative to the upper and lower teeth.

As described above in connection with FIGS. 1*a*-1*d*, a part 71 is drawn on a canvas which consists of two arches of teeth, upper and lower. On those teeth, we define a set of magnet points 72. These are the places at which a part 71 can be positioned as shown by the solid dots in FIGS. 17*a* and 17*b*. Each magnet point 72 has a code that indicates its location on the canvas—its x and y location on the screen and its position related to the teeth—i.e., whether it is on the upper or lower, lingual, labial, or buccal, and so forth.

Figure 18:
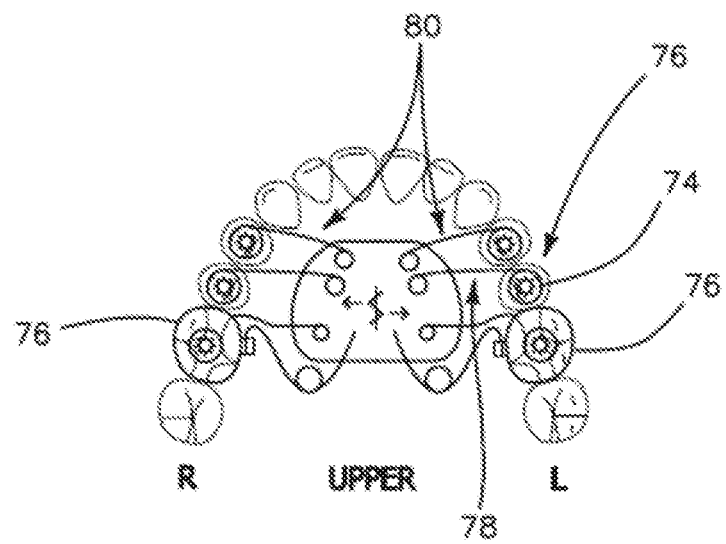
FIG. 18 is a diagram that depicts a design for an orthodontic appliance for an upper set of teeth.

In FIG. 18 each circle 74 is called an anchor 76. Anchors 76 sit on magnet points 72. They are handles that the user can grab to manipulate the part 71. The part 71 can be a bracket, a wire, a pad, a retainer plate or any other kind of dental or orthodontic component. The user clicks on the circle 74 with the mouse and drags the circle 74 to another tooth. The user can also right click and is presented with a list of options that are available to modify the part 71. The anchors 76 are the handles the user grabs to reconfigure the part 71.

Figure 19:
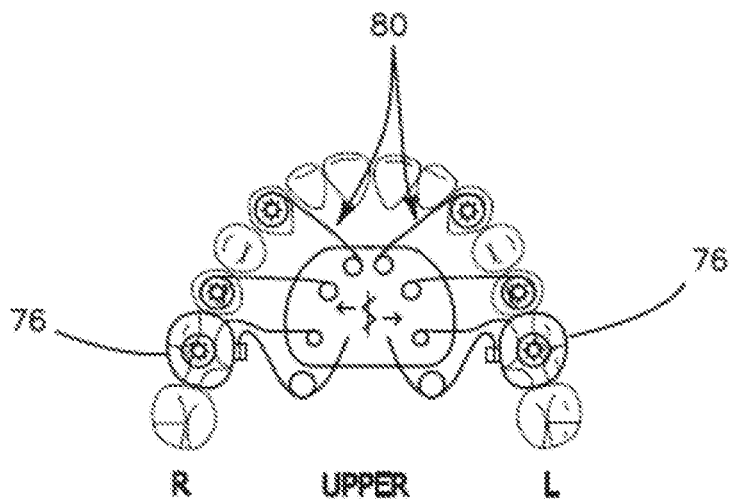
FIG. 19 is the diagram of FIG. 18 wherein the design has been modified using the domain specific language (DSL) of the illustrated embodiments.

FIG. 19 shows the situation where a part 71 that has been reconfigured from the configuration shown for example in FIG. 18. One sub-component 78 in FIG. 18 has been removed, and two others 80 have been moved. Parts can only be reconfigured in very specific ways—e.g., with this part 71 the two anchors 76 toward the back of the mouth cannot be removed or moved. If the user tries to modify them, EasyRx will not allow it. All of these behaviors are defined in the DSL, and EasyRx uses the DSL to put boundaries on the user's manipulation of the parts.

The configurations of FIGS. 17 and 18 is a very simple scenario. EasyRx allows more complex movements and relationships. For example, relationships between anchors 76 can be established whereby one anchor's movement will cause another anchor 76 to move in a given way. Furthermore, the drawing on the canvas can change as an anchor 76 moves from one magnet point 72 to another. Internal system rules are defined to define realities about the parts themselves and how they are used in orthodontic treatment.

Turn now and consider an overview of the DSL implementation. There are two aspects to the EasyRx parts DSL. One allows for the definition of the parts and their behaviors, and the other allows for the application to draw those parts on the canvas and respond to user commands for alteration of the part configuration.

Consider first the DSL and how it defines behaviors. We provide a set of rules into EasyRx for each part 71. When these rules are provided, EasyRx recognizes the existence of the part 71, and allows the user to create a prescription or rule set with it. The rules define the part's behavior, and are specified using the DSL. An example of what the rule for one part 71 looks like in pseudo-code is set forth below.

```
behavior: {
  anchors: [
    0: {
      which_teeth: 4-7,
      side: UL,
      starting_location: 6UL,
      color: Green,
      which_drawing: 9032,
    },
    1: {
      which_teeth: 4-7,
      side: UR,
      starting_location: 6UR,
      color: Green,
      which_drawing: 9032,
    },
  ],
  anchor_buddies_allowed_positions: [
```

-continued

```
{
  anchors_buddy: 0 → 1,
  rules: {
    1: [1], 2: [2, 1], 3: [3, 2], 4: [3], 5: [4]
  }
  }
  }
  ],
  forced_move: [ ... ],
  anchors_pair_across_arch: [ ... ]
},
options: {
  transform: { ... },
  transform_1: { ... },
  transform_2: { ... },
  transform_3: { ... },
    ...
  transform_9: { ... },
  color: { ... },
},
place: function ( ) { ... },
update: function ( ) { ... }
```

Note the behavior section, which defines what anchors 76 a part 71 has, what drawings are associated with each anchor 76, how and to where the anchor 76 moves, and how its movements affect other anchors 76.

First we define the set of anchors 76 that comprise the part 71. Each anchor 76 has a range of magnet points 72 it can sit on or at which it can be positioned. For example, we might define an anchor 76 that can sit on all the upper arch magnet points 72 on teeth 1-4 (counting from the front of the mouth back). We then associate a drawing with that anchor 76, one for each position that the anchor 76 can sit in. Along with the anchor definition, we define the color of the drawing associated with that anchor 76. Finally, we also define whether the anchor 76 can be removed. This allows subparts of parts 71 to be pulled off the canvas.

If we need to have one anchor's position influence another anchor's position, we define that relationship next by setting up forced moves 82, anchor buddies 84 and anchor pairs 86. Each one establishes a different relationship between the anchors 76. Forced moves 82 allow any anchor 76 to be moved to a specific magnet point 72 when the current anchor 76 is on a specific magnet point 72. Anchor buddies 84 are used to keep the positions of two anchors 76 within a certain distance of each other. Anchor pairs 86 are used to pair two anchors 76 across the arch 88, one on the left side and one of the right side. When the left side moves to a certain magnet point 72, the right side will be moved with it.

Figure 20A:
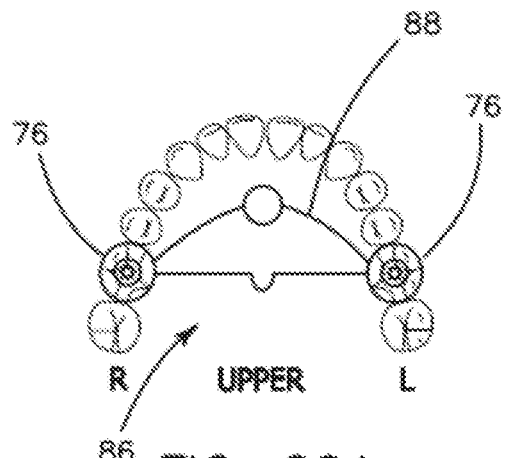
FIGS. 20a and 20b are diagrams showing the modification of another design using the domain specific language (DSL) of the illustrated embodiments.
Figure 20B:
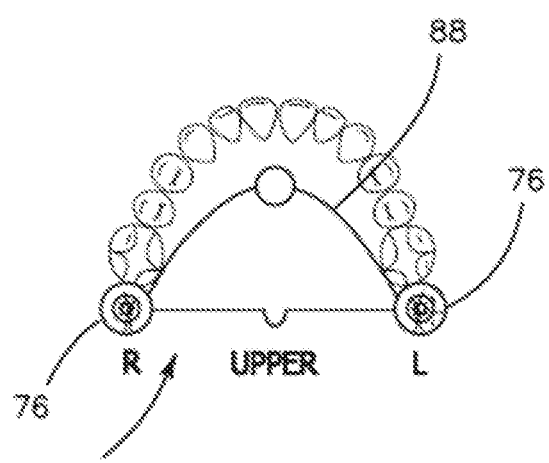

FIGS. 20a and 20b illustrate an example of a part 71 with anchors 76 paired across the arch 88 in an anchor pair 86. Whenever the anchor 76 on the left or right is moved, the anchor 76 on the other side is moved with it as shown by comparison of FIG. 20a to FIG. 20b.

Figure 21A:
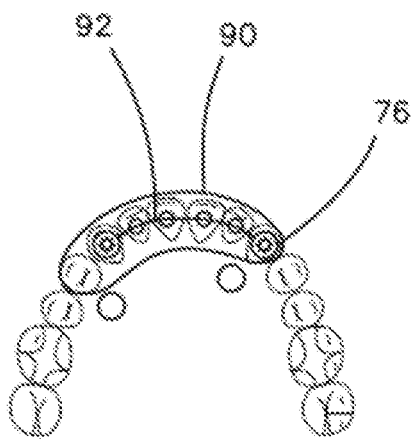
FIGS. 21a and 21b are diagrams showing the modification of yet another design using the domain specific language (DSL) of the illustrated embodiments.
Figure 21B:
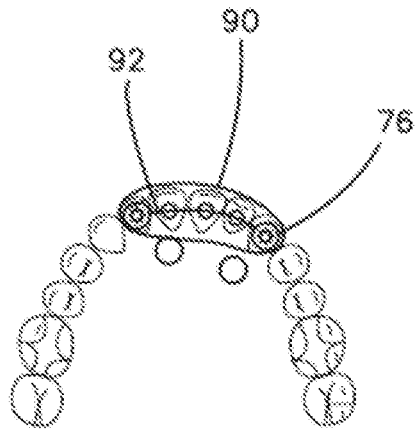

FIGS. 21a and 21b is an example of anchor buddies 84. Whenever the anchor 76 that controls the tray 90 is moved the wire 92 moves too, and vice versa as can be verified by comparison of FIG. 21 a and FIG. 21b, where one tooth has been removed from tray 90. This is done because the tray 92 contains the wire 92 within it.

Figure 22:
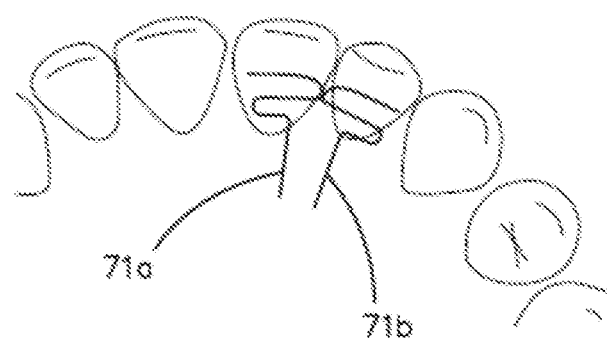
FIG. 22 is a diagram showing the transformation of a part between two different orientations of a design using the domain specific language (DSL) of the illustrated embodiments.

The second aspect handles transformations of the part's appearance on the canvas or its orientation with respect to the teeth or other parts. For example, certain parts flip across the x axis, and those flips are defined here. In FIG. 22, the part 71a on the right is the same as the left part 71b, but it has been transformed with an optional flip to make it face the opposite way.

The transformations are defined by specifying to which of the parts' anchors 76 the transform applies and the setting the result of the transformation, e.g., whether the transform removes the anchor 76, changes the drawing, or something else.

Consider now the DSL movement. The final two lines in the listing of psuedocode above, "place" and "update", control the part's movements while the user is interacting with the part 71. The function codes "place" and "update" consume the behavior rules, draw the images on the canvas, and create the listeners or receiving software modules to respond to user input. Whenever a user moves one of the anchors 76, the update function checks the rule set, which we make executable for performance, and if any changes need to be made, e.g., if an anchor 76 was moved and as a result an anchor buddy 84 needs to be moved, the update function makes those changes. The update function also prevents the user from putting an anchor in a place it cannot be placed according to the behavior section of the part's definition.

Consider the significance of the DSL. Using this method, we define 355 or more different orthodontic parts. As part of that definition we have a catalog of how all those parts behave. We can ask, for example, whether a given part 71 can ever be placed on a certain tooth. Or if we place the left side of the part 71 on a given tooth, on what teeth it is allowed to be placed across the arch 88 on the right side. Essentially, it is a taxonomy of orthodontic parts with the rules for their behavior. This set of rules has utility beyond EasyRx. It can be used by any software that needs to place orthodontic parts on teeth and needs to know which teeth can receive which parts. It is not tied to any specific method of display.

In another embodiment, the user has the ability to create a dental prescription which goes beyond those used for orthodontic purposes. Specifically, the dental prescription created by the system may include crowns, bridges, implants, abutments, rests, major connectors, and/or dentures or any other dental appliances now known or later devised. Using the dental prescription workspace 100 depicted in FIG. 23, the user can create the prescription by interacting with the various graphical interfaces disposed therein.

For example, after the user has selected which dental part is to be added to a prescription, that part is listed under the part options heading 102 within the dental prescription workspace 100. The user then selects which tooth to apply the dental part by selecting the corresponding icon within the dental prescription area 104. The user then has the ability to adjust or select a number of features or options associated with that specific dental appliance. In the exemplary embodiment seen in FIG. 23 where a crown has been chosen, the user is presented with the ability to set the shade of the crown in the shade box 106, the color of the stump in the stump shade box 108, and the shade of the characteristics in the characteristics box 110. Additionally, the margin of the crown may be selected from a plurality of different options presented in the margins box 112, while the pontic of the crown may be chosen from the plurality of options within the pontic box 114. The user may add additional customization options for the selected dental part by actuating the "Add New Product Option" box 116 and then progressing through a plurality of sub windows.

Figure 23:
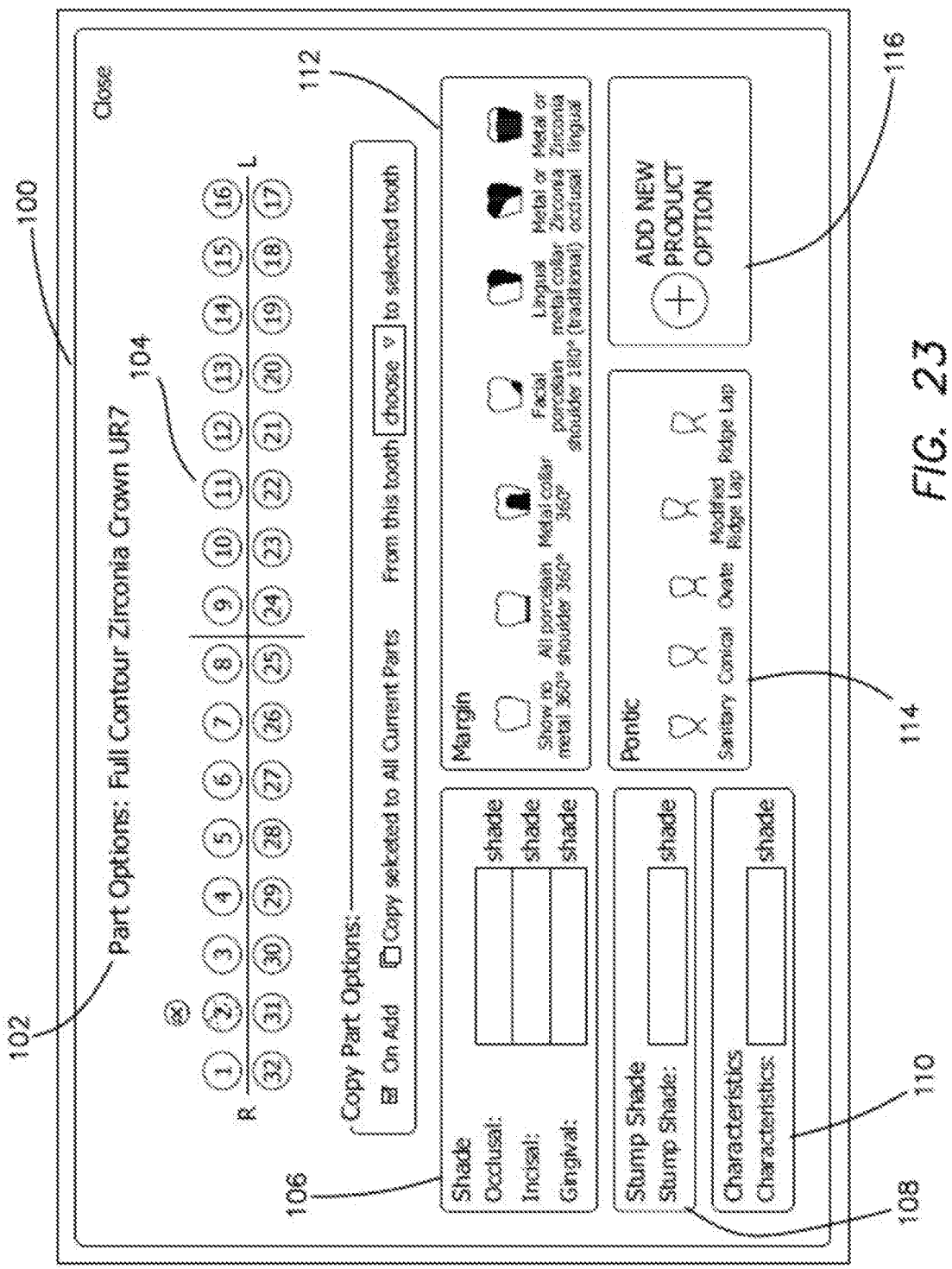
FIG. 23 is an illustrative example of a screen shot of the dental prescription workspace of the illustrated embodiment.

It should be noted that the dental prescription workspace 100 seen in FIG. 23 is meant to be for illustrative purposes only and that different customization options may appear within the dental prescription workspace 100 for different selected dental appliances. For example, the customization options such as the shade box 106 or the margins box 112 may be present only when a crown is the selected dental appliance as displayed in the part options heading 102 and that additional, analogous, or different customization options may be present within the dental prescription workspace 100 when a different dental appliance, such as dentures, is selected. In this fashion, the dental prescription workspace 100 presents only those customization options which are the most relevant or appropriate according to which dental appliance is selected by the user to be added to the overall prescription.

As discussed in context with a previous embodiment, since everything on the dental prescription workspace 100 is digital relating to the parts and options which are selected from the plurality of option boxes 106-116 available, everything has a price attached to it so in essence, the designer of a case is also simultaneously billing the case as the steps of making the design are performed, thereby eliminating the need to have billing manually performed separately by another worker. For example, if the prescribing user selects "Lingual Metal Collar" from the margins box 112, the billing is automatically updated to reflect the specific pricing for fabricating a crown with that specific option selected. The user has full control over the parts within the system, e.g. the user can change the price as well as how the parts present themselves in the parts library for those working within the workspace through the use of the Manage Parts module 70 as shown in FIG. 16.

In yet another embodiment, the current invention allows a user to track the manufacturing workflow for aligner cases. As discussed above and shown in FIG. 10, a prescription for a sequence of clear aligners may be produced by the user picking which teeth to move and then selecting how many trays are to be used over the duration of the prescription, the final prescription then being uploaded to a lab while also simultaneously being added to an invoice or bill for the patient.

As is known in the art, an aligner prescription consists of a number of aligner trays which are worn at scheduled intervals. For example, the user develops a treatment plan for the patient who needs to wear 20 aligner trays on their upper teeth and 20 on their lower teeth, thereby requiring a total of 40 trays. When a patient begins treatment, often not all 40 trays are delivered to the patient and instead the patient receives aligners in "batches" or "groups." Clinicians set their preferred protocol for delivering trays. For example, a the user clinician may deliver 7 upper trays and 7 lower trays when the patient begins treatment and then delivers additional trays as their treatment progresses.

The current invention provides an aligner tracking workspace 120 as seen in FIG. 24 which allows the user to more closely to monitor treatment and patient cooperation and to further make any necessary adjustments to the treatment plan. Once a patient record and a lab is selected, the relevant patient information 122 and lab information 124 are displayed near the top of the aligner tracking workspace 120. The aligner tracking workspace 120 further comprises a plurality of inputs which allow the user to track the progress of the patient's aligner treatment. Specifically, the user may adjust the length of the overall aligner treatment by inputting the total number of trays needed for both the upper and lower teeth through the total upper input 126 and the total lower input 128, respectively. The total tray output 130 automatically displays the total number of trays required for the ordered prescription. Similarly, the user may set the number of trays used in each batch through the batch upper input 132 and the batch lower input 134. The total batch output 136 automatically displays the total number of trays required for the currently selected batch.

The tray printed status windows 138 display the number of trays for the upper teeth, the lower teeth, and the total number of trays which have been printed for a selected batch, while the tray delivered status windows 140 displays the number of trays for the upper teeth, the lower teeth, and the total number of trays which have been delivered for a selected batch. Relatedly, the delivery date window 146 displays the specific date in which all of the trays of the selected batch were delivered to the patient.

In the tray duration window 142, the number of days or length each pair of upper and lower trays should be used is displayed. The batch duration window 144 in turn displays the total number of days or length of time that the batch of aligners currently being reviewed in the aligner tracking workspace 120 should be used by the patient. The batch duration window 144 may be populated directly by the user, or alternatively, the batch duration window 144 may be automatically populated when entries are made in the other fields within the aligner tracking workspace 120. For example, as seen in FIG. 24, when the user determines that the batch includes nine trays for the upper and lower teeth using the batch upper input 132 and the batch lower input 134, respectively, and further indicates that each tray should be used for seven days in the tray duration window 142, the underlying algorithm running the aligner tracking workspace 120 will automatically calculate and display the total length of time the current batch should be used by the patient within the batch duration window 144 which in this instance is 63 days, i.e. nine trays multiplied by seven days each.

FIG. 24 also shows a finish date window 148 which displays the projected date in which the currently selected batch will be completely used by the patient according to the recommended prescription. Similar to the batch duration window 144 discussed above, the finish date window 148 may be populated by the user directly or through the entry of other inputs contained within in the aligner tracking workspace 120. For example, if a total of 63 days is displayed within the batch duration window 144, the underlying algorithm running the aligner tracking workspace 120 will automatically calculate and display the projected end use date for the currently selected batch within the finish date window 148 which in this instance is "Jan. 18, 2020", i.e. 63 days from the displayed date of "Nov. 16, 2019" within the delivery date window 146.

The aligner tracking workspace 120 further includes a plurality of reminder windows which may display dates, lengths of time, or other information related to batch of aligners currently being used or delivered to the patient. In FIG. 24, a first reminder window 150 and a second reminder window 152 may be seen however it is to be expressly understood that fewer or additional reminder windows may be viewed and interacted with within the aligner tracking workspace 120 without departing from the original spirit and scope of the invention. It can also be seen in FIG. 24 that the first reminder window 150 displays the date in which the user should implement or begin the printing of the next or subsequent batch of aligners within the patient's overall prescription while the second reminder window 152 displays the date in which the user should contact the patient and schedule a follow up appointment. Like with the information displayed in the first and second reminder windows 150, 152 themselves, it should be noted that what the information displayed relates to can also be varied from what is explicitly seen and described within FIG. 24. In other words, the specific reminders seen in the figure are meant to be illustrative purposes only and that different reminders may be used in their stead without changing the overall scope of the current invention.

The aligner tracking workspace 120 further comprises a trays remaining block 156 which displays the number of remaining trays to be printed and delivered to the patient in order to complete their prescription. Specifically, the trays remaining block 156 displays the number of upper trays, the number of lower trays, and the overall total number of trays remaining within the patient's prescription beyond those trays within the batch that is currently under review in the aligner tracking workspace 120. Finally, a save batch button 154 is present which allows the user to save the settings for the current batch and move on to another or different batch or to return to another aspect of the larger prescription system discussed above.

Everything within the aligner tracking workspace 120 including the parts and options which are selected from the plurality of option boxes 126-156 has a price attached to it. Therefore as the prescribing user is using the aligner tracking workspace 120 for a case, they are also simultaneously billing the case as the steps of assigning the plurality of trays are performed, thereby eliminating the need to have billing manually performed separately by another worker. For example, if the prescribing user determines that 18 of the 40 aligner trays consisting of the patient's entire prescription are to be part of "Batch #1" using the batch upper input 132 and the batch lower input 134 seen in FIG. 24, the billing is automatically updated to reflect the specific pricing for fabricating those specific trays as that specific option is selected. The user has full control over the parts within the system, e.g. the user can change the price as well as how the parts present themselves in the parts library for those working within the workspace through the use of the Manage Parts module 70 as shown in FIG. 16.

It is a further aspect of the current invention to provide a means for the user to interact with the prescription system as described above through a series of voice or audio commands. In this embodiment, the user may use and navigate through any feature of the current invention including but not limited to the practice dashboard 10, the prescription workspace 22, and/or the dental prescription workspace 100 by saying an appropriate keyword or phrase as detected by speech detection software as is known in the art. Specifically, a microphone, speaker, or other transducer is coupled to the system operating the web based application of the current invention and is configured to cooperate with the system so that a user may interact with the prescription management system at least in part through just their vocal commands and thereby dictate the patient prescription.

In one particular example, the user may issue a series of vocal or audio commands in order to produce a prescription for a dental or orthodontic appliance by first selecting a pre-existing patient by stating "Lookup patient John Doe, date of birth Jul. 27, 2011, choose "The Williams Lab" to send the case." The system then responds by searching through the patient tab 12 and then displaying the corresponding patient's profile to the user as seen in FIG. 3. Next, the user may begin building a dental or orthodontic prescription for the patient by issuing a series of audio command such as "Prescribe a Hawley retainer upper and lower", "Move the labial bow 3 to 3 with wire gauge point 28", and/or "Set acrylic color to red on lower and blue on the upper" which causes the system to move the user back and forth through system including the prescription workspace 22 seen in FIGS. 4 and 6-10 and carry out or implement their corresponding commands. The user may also navigate through the aligner tracking workspace 120 with any number or different types of audio commands for example by saying "Set date needed as Dec. 17, 2020." The user may then conclude the prescription by stating "Create prescription, set for review" which indicates to the system to save the prescription created by the user and/or upload the prescription to the previously selected lab.

In a related embodiment, the system may also be used to request that a specific prescription be remade or to have a portion of a previously prepared prescription repaired. For example, the upload tab 46 shown in FIG. 11 may further comprise the option to resubmit a previously prepared and saved prescription using the same lab and same options previously input by the user. Additionally, the upload tab 46 further comprises the option to request that a specific portion or appliance which is part of the overall prescription to be repaired. Here, the user may select the part or parts requiring repair listed within the upload tab 46 and then send a request to the preselected lab to repair or remake only that specific appliance using the original parameters as specified in the original prescription.

The illustrated embodiments of the system and method can now be understood as an overall prescription management system and method designed to run the logistics of an orthodontic lab while allowing doctors access to submit, store, and review all their prescriptions. The system allows for flexibility to make customizations based on the particular lab using the system. Multiple users of the system provide input through prescription, design and fabrication phases, which activities simultaneously creates a digital tracking and document record of the case and automatic billing. Since this is a web based system, updates can be made on the fly and the labs' data as well as the doctors' data is stored via the cloud.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method for using a prescription management network directly communicating a dental lab with a prescribing user, the method comprising:

creating a digital graphical representation in a computer of a patient's teeth by the prescribing user;

creating a digital prescription for a customized dental appliance by the prescribing user applying a plurality of dental components to the digital graphical representation of a patient's teeth in a computer;

selecting a plurality of options associated with each of the plurality of dental components within the customized dental appliance;

submitting the digital prescription and the digital graphical representation of a patient's teeth by the prescribing user directly from the prescribing user's computer to the dental lab through the network;

storing the digital prescription in a cloud-based database accessible by both the prescribing user through the prescribing user's computer and by the dental lab through the dental lab's computer;

accessing the digital prescription by the dental lab through the dental lab's computer to design the customized dental appliance;

fabricating the designed customized dental appliance by the dental lab at the dental lab from a predefined parts library;

tracking the fabrication of the customized dental appliance by the prescribing user or by the dental lab by updating the cloud-based database; and simultaneously creating at the dental lab's computer an automatic billing and storing the automatic billing in the cloud-based database at the same time the digital prescription is created by the prescribing user, when the plurality of options associated with each of the plurality of dental components within the customized dental appliance are selected, when the digital prescription is submitted directly to the dental lab by the prescribing user, when the digital prescription is stored, when the customized dental appliance is designed by the dental lab, or when the designed customized dental appliance is fabricated by the dental lab, regardless of whether initiated through either the prescribing user's or the dental lab's computer, wherein simultaneously creating the billing and storing the billing in the cloud-based database at the same time the digital prescription is created by the prescribing user comprises creating an itemized queue of the applied plurality of dental components and their respective pricing automatically through either the prescribing user's or the dental lab's computer in real time as each dental component is applied to the digital graphical representation of the patient's teeth by the prescribing user, and wherein simultaneously creating the billing and storing the billing in the cloud-based database at the same time the plurality of options associated with each of the plurality of dental components within the customized dental appliance are selected creating an itemized queue of the selected plurality of options and their respective pricing automatically through either the prescribing user's or the dental lab's computer in real time as each option associated with a dental component is selected by the prescribing user.

2. The method of claim 1 wherein selecting a plurality of options associated with each of the plurality of dental components within the customized dental appliance comprises:

selecting a shade associated with at least one of the plurality of dental components;

selecting a margin associated with at least one of the plurality of dental components; or selecting a pontic associated with at least one of the plurality of dental components.

3. The method of claim 2 wherein selecting a shade associated with at least one of the plurality of dental components comprises selecting an occlusal, an incisal, a gingival, a stump, or a characteristic shade.

4. The method of claim 1 further comprising creating a customized option associated with at least one of the plurality of dental components within the customized dental appliance.

5. The method of claim 1 wherein each of the steps are performed by issuing a plurality of voice commands by the prescribing user.

6. The method of claim 1 wherein creating a digital graphical representation in a computer of a patient's teeth by the prescribing user comprises acquiring a three dimensional scan of the patient's teeth and applying the three dimensional scan to the digital graphical representation in the computer.

7. The method of claim 1 wherein creating a digital prescription for a customized dental appliance by the prescribing user applying a plurality of dental components to the digital graphical representation of a patient's teeth in a computer comprises creating a three dimensional digital prescription for the customized dental appliance.

8. A method of providing an orthodontic aligner prescription tracking management network comprising an orthodontic or dental lab and at least one prescribing user, the method comprising:

providing a digital aligner tracking workspace in a computer wherein the orthodontic or dental lab or the at least one prescribing user may access the digital aligner tracking workspace;

creating a digital prescription for a customized orthodontic aligner appliance by the prescribing user for a patient's teeth in a computer, the digital prescription comprising a plurality of trays;

storing the digital prescription in a cloud-based database selectively accessible by the orthodontic or dental lab and the at least one prescribing user;

tracking and storing a record of the status of the digital prescription for the customized orthodontic aligner appliances;

updating the digital prescription by either the orthodontic or dental lab or the at least one prescribing user; and simultaneously creating a billing in the cloud-based database at the same time the digital prescription for the customized orthodontic aligner appliance is created by the prescribing user for a patient's teeth in the computer, when the digital prescription is stored, or when the digital prescription is updated, regardless if updated by either the orthodontic or dental lab or the at least one prescribing user, wherein tracking and storing a record of the status of the digital prescription for the customized orthodontic aligner appliances comprises automatically updating the record of the status of the digital prescription according to any updates made to the digital prescription by either the orthodontic or dental lab or the at least one prescribing user.

9. The method of claim 8 wherein tracking and storing a record of the status of the digital prescription for the customized orthodontic aligner appliances comprises tracking and storing an amount of trays selected from the plurality of trays to be within a first batch, while simultaneously tracking and recording which of the plurality of trays are designated for the upper teeth and lower teeth of the patient, respectively.

10. The method of claim 9 wherein tracking and storing a record of the status of the digital prescription for the customized orthodontic aligner appliances comprises tracking which of the plurality of trays selected to be within the first batch have been printed by the orthodontic or dental lab.

11. The method of claim 9 wherein tracking and storing a record of the status of the digital prescription for the customized orthodontic aligner appliances comprises tracking which of the plurality of trays selected to be within the first batch have been delivered to the patient.

12. The method of claim 8 wherein updating the digital prescription by either the orthodontic or dental lab or the at least one prescribing user comprises adjusting a duration for each of the plurality of trays to be used by the patient, and wherein automatically updating the record of the status of the digital prescription according to any updates made to the digital prescription by either the orthodontic or dental lab or the at least one prescribing user comprises automatically updating a total duration that the plurality of trays will be used by the patient according to the adjusted duration for each of the plurality of trays.

13. The method of claim 12 further comprising automatically generating a reminder to begin printing a sub-plurality of the plurality of trays according to the updated total duration that the plurality of trays will be used by the patient.

14. A prescription management system comprising an orthodontic or dental lab and a plurality of prescribing users, the system further comprising:

means for creating a plurality of prescriptions by applying at least one dental appliance to a graphical representation of a patient's teeth by each of the plurality of prescribing users, each of the plurality of prescriptions comprising at least one dental appliance;

a cloud-based database configured to receive the plurality of prescriptions directly from the plurality of prescribing users, wherein the cloud-based database is selectively accessible by both the plurality of prescribing users and by the orthodontic or dental lab; and a digital workspace configured to provide the orthodontic or dental lab or the plurality of prescribing users the ability to customize the at least one dental appliance within each of the plurality prescriptions by selecting from a plurality of corresponding options for the at least one dental appliance, wherein the cloud-based database is configured to store the plurality of prescriptions, wherein the cloud-based database is configured to track and store a record of fabrication of the at least one customized dental appliance for each of the plurality of prescriptions by the orthodontic or dental lab, and wherein the digital workspace is configured to simultaneously create a plurality of corresponding billings in the cloud-based database at the same time the plurality of prescriptions are created by the plurality of prescribing users, when the plurality of prescriptions are submitted directly by the plurality of prescribing users, when the plurality of corresponding prescriptions are stored, when the at least one dental appliance for each of the plurality of prescriptions is customized, or when the at least one dental appliance for each of the plurality of prescriptions is fabricated at the orthodontic or dental lab, regardless if initiated by either the orthodontic or dental lab or the plurality of prescribing users, wherein the digital workspace being configured to simultaneously create the plurality of corresponding billings in the cloud-based database at the same time the plurality of prescriptions are created by the plurality of prescribing users comprises the digital workspace further being configured to create an itemized queue of the at least one applied dental appliance and its respective pricing automatically as the at least one dental appliance is applied to the graphical representation of the patient's teeth by each of the plurality of prescribing users for each of the plurality of corresponding prescriptions, wherein the digital workspace configured to provide the orthodontic or dental lab or the plurality of prescribing users the ability to customize the at least one dental appliance within each of the plurality prescriptions by selecting from a plurality of corresponding options for the at least one dental appliance comprises:

means for selecting a shade associated with at least one of the plurality of dental components;

means for selecting a margin associated with at least one of the plurality of dental components; or means for selecting a pontic associated with at least one of the plurality of dental components.

15. The prescription management system of claim 14 where the means for selecting a shade associated with at least one of the plurality of dental components comprises means for selecting an occlusal, an incisal, a gingival, a stump, or a characteristic shade.

16. The prescription management system of claim 14 further comprising means for creating a customized option associated with at least one of the plurality of dental components within the customized dental appliance.

17. The prescription management system of claim 14 further comprising means for issuing a plurality of voice commands by the prescribing user.

18. The prescription management system of claim 14 wherein the means for creating a plurality of prescriptions by applying at least one dental appliance to a graphical representation of a patient's teeth by each of the plurality of prescribing users comprises means for applying at least one dental appliance to a three dimensional scan of the patient's teeth.

19. The prescription management system of claim 14 wherein the means for creating a plurality of prescriptions by applying at least one dental appliance to a graphical representation of a patient's teeth by each of the plurality of prescribing users comprises means for creating a plurality of three dimensional digital prescriptions by applying at least one dental appliance to a three dimensional scan of the patient's teeth.

\* \* \* \* \*